United States Patent
Bao

(10) Patent No.: US 10,466,200 B2
(45) Date of Patent: Nov. 5, 2019

(54) GEL ELECTROPHORESIS CHIP

(71) Applicant: Jian-Bin Bao, Edmonton (CA)

(72) Inventor: Jian-Bin Bao, Edmonton (CA)

(*) Notice: Subject to any disclaimer, the term of this patent is extended or adjusted under 35 U.S.C. 154(b) by 373 days.

(21) Appl. No.: 15/520,466

(22) PCT Filed: Oct. 20, 2015

(86) PCT No.: PCT/CN2015/092242
§ 371 (c)(1),
(2) Date: Apr. 20, 2017

(87) PCT Pub. No.: WO2016/062231
PCT Pub. Date: Apr. 28, 2016

(65) Prior Publication Data
US 2017/0315089 A1 Nov. 2, 2017

(30) Foreign Application Priority Data

Oct. 21, 2014 (CN) .......................... 2014 1 0563444

(51) Int. Cl.
*G01N 27/447* (2006.01)
*C07K 1/28* (2006.01)

(52) U.S. Cl.
CPC ....... *G01N 27/44747* (2013.01); *C07K 1/285* (2013.01); *G01N 27/44791* (2013.01)

(58) Field of Classification Search
CPC ....... G01N 27/44747; G01N 27/44791; G01N 27/447; C07K 1/285
See application file for complete search history.

(56) References Cited

U.S. PATENT DOCUMENTS

| | | | |
|---|---|---|---|
| 2007/0178463 A1 | 8/2007 | Tanaami | |
| 2010/0213065 A1* | 8/2010 | Astrom | C07K 1/14 204/459 |

FOREIGN PATENT DOCUMENTS

| | | |
|---|---|---|
| CN | 102504010 | 6/2012 |
| CN | 103122311 | 5/2013 |
| CN | 104359962 | 2/2015 |
| WO | 2010/053443 | 5/2010 |

OTHER PUBLICATIONS

International Search Report filed in PCT/CN2015/092242 dated Jan. 18, 2016.

* cited by examiner

*Primary Examiner* — J. Christopher Ball
(74) *Attorney, Agent, or Firm* — Rankin, Hill & Clark LLP

(57) ABSTRACT

The present invention discloses a gel electrophoresis chip, comprising a first substrate, a first plurality of parallel gel strips formed on the first substrate, respectively extending along a first direction and having a certain width; and a second plurality of isolation segments formed on the first substrate, respectively located between adjacent gel strips and extending along a second direction different from the first direction, the isolation segments being arranged to form a microwell array together with the gel strips. After the gel electrophoresis chip achieves conventional protein two-dimensional gel electrophoretic separation, protein samples suitable for mass spectrometry analysis are prepared in high throughput, thus greatly reducing the pretreatment time of mass spectrometry analysis, thereby being suitable for proteomic analysis of biological samples.

20 Claims, 8 Drawing Sheets

GEL ELECTROPHORESIS CHIP

TECHNICAL FIELD

The present invention relates to the field of protein electrophoresis, in particular to a gel electrophoresis chip.

BACKGROUND

With the implementation and progress of the Human Genome Project, life science research has entered the post-genome era. In this era, life science turns to focus on proteins because the whole-genome sequence information is insufficient to explain or speculate various life phenomena, but proteins play a significant role in executing the physiological functions and directly reflect life phenomena, hence researches on the structure and function of proteins will directly explain the mechanism of changes of life under physiological or pathological conditions before and after drug intervention.

In the proteomic analysis of a biological sample, in order to determine the types of proteins contained in the biological sample or find out a target protein of interest, first of all, it is necessary to separate proteins in the biological sample. The existing two-dimensional gel electrophoresis analysis method can separate proteins in a biological sample in two dimensions. Typically, the method involves firstly separating proteins in the first dimension by isoelectric focusing electrophoresis (first-dimensional electrophoresis) based on the difference in protein isoelectric point, and then separating the proteins resulting from the first-dimension separation in the second dimension by polyacrylamide gel electrophoresis (second-dimensional electrophoresis) based on the difference in protein molecular weight. After the separation of second-dimensional electrophoresis, the separated proteins on the gel are stained, so that the proteins in the gel are visualized in the form of protein spots. Due to the differences in isoelectric point and molecular weight, different proteins are located in different positions of the gel. For a biological sample, there are tens of thousands of protein spots or even more. In order to identify proteins in the protein spots, it is necessary to excise the gel containing the protein spots (i.e., gel excision). Then the proteins are digested in the gel (i.e., in-gel digestion) to form peptide mixtures, and the peptide mixtures are extracted. Finally the peptide mixtures are made into sample targets (i.e., target preparation) by different mass spectrometry (MS) ionization methods, followed by MS analysis to obtain MS information of the proteins, such as peptide mass fingerprinting and peptide sequence tag. Thus, before MS analysis, the proteins separated by the second-dimensional electrophoresis need to undergo the sample preparation mentioned above, including staining, gel excision, in-gel digestion, peptide mixture extraction and target preparation. All the protein spots to be detected need to undergo the steps of gel excision, in-gel digestion, peptide mixture extraction and target preparation, such operation is feasible for the detection of a small amount of protein spots. However, as a biological sample contains a huge number of protein spots, it is time-consuming and laborious for the sample preparation of each protein spot. Even with automatic gel excision instruments, automatic enzymatic digestion instruments and automatic target making instruments, it is difficult to treat all protein spots on the gel one by one. Thus, it is urgent for proteomic analysis of biological samples to simplify the operations of second-dimensional electrophoresis and pretreatment before MS analysis and after electrophoresis.

Biochip technology provides the possibility, for example, microfluidic chip technology has been widely used in the field of proteomic analysis: a combination of isoelectric focusing and capillary electrophoresis (A. E. Herr et al., Anal. Chem., 75, 1180-1187, 2003), a combination of isoelectric focusing and capillary electrophoresis (Y. Li et al., Anal. Chem., 76, 742-748, 2004), and an integration of capillary electrophoresis, fractionation, solid phase extraction and electrospray ionization (ESI) (Q. Y. Lu, J.-B. Bao, D. J. Harrison, $11^{th}$ Int. Conf. Miniatur. Syst. Chem. Life Sci., p. 44-46, 2007), etc.

However, at present, these attempts still do not meet the need for rapid preparation of a large number of samples in proteomic analysis, and a more practical microchip technology is required for proteomic analysis.

SUMMARY OF THE INVENTION

The object of this invention is to provide a gel electrophoresis chip, within which realized are sample preparation steps for the mass spectrometry analysis of a biological sample, including protein separation, in-gel digestion, peptide mixture extraction, and target fabrication, etc. By the invention, one may omit the steps of gel staining and gel excision in the existing sample preparation process and makes the time required for the digestion, peptide mixture extraction and target preparation of all proteins in a biological sample substantially the same as the time required for the digestion, extraction and target preparation of one protein spot in the prior art. Thus, the time required for MS sample preparation of a to-be-detected biological sample containing a large number of proteins is greatly shortened, the complicated sample preparation process is simplified, therefore, the large-scale high-throughput sample preparation required for proteomics is provided for proteomic analysis of biological samples.

In order to achieve the objective of the present invention, the present invention provides the technical solution as follows:

a gel electrophoresis chip, comprising:

a first substrate;

a first plurality of gel strips formed on the first substrate, respectively extending along a first direction and having a certain width, the gel strips being lanes for protein separation;

a second plurality of isolation segments formed on the first substrate, respectively located between adjacent gel strips and extending along a second direction different from the first direction, the isolation segments being arranged to form a microwell array together with the gel strips.

Preferably, the second direction is perpendicular to the first direction.

Preferably, the gel electrophoresis chip further comprises a second substrate located on the gel strips and the isolation segments and in contact with the gel strips and the isolation segments.

Preferably, the gel electrophoresis chip further comprises a plurality of isolation strips respectively formed on the same side of the individual gel strips, in contact with the gel strips and having substantially the same thickness.

Preferably, the gel electrophoresis chip further comprises isolation strips formed on both sides of each gel strip, in contact with the gel strips and having substantially the same thickness, the isolation strips each have at least one opening at each microwell, and the opening serves as a channel for electric current and a channel through which protein or peptide mixtures enter the microwell.

The gel strips in the gel electrophoresis chip are used for protein separation, including but not limited to polyacrylamide gel strips, agar or agarose gel strips, or starch gel strips, and the way they are polymerized and their formulations selected are the same as those for the conventional bulk gels. The gel strips are used for the second-dimension separation in two-dimensional gel electrophoresis, the overall width of which preferably matches the length of immobilized pH gradient (IPG) strips of the first-dimension gel electrophoresis. The overall size of the chip formed by all of the gel strips, microwells, isolation segments and isolation strips may be the same as that of the conventional bulk gel.

Preferably, the width of the gel strips is 1 μm-1 cm, more preferably 10 μm-2 mm.

Preferably, the isolation segments and the isolation strips are made of one or more materials selected from an inorganic material, an organic material, a polymer material and a composite material, preferably, the polymer material is selected from resins, rubbers, fibers, plastics, photoresists, adhesive or paint, and the isolation strips and the isolation segments may be of the same or different material. The isolation segments for forming the microwell array and the isolation strips formed on the side of the gel strips cannot adsorb or separate proteins, so that the proteins that are transferred from the gel strips to the microwells are retained in the microwells. After the proteins are separated or the separated proteins are digested in the gel, the proteins or peptide mixtures are transferred from the gel to the microwells by applying a voltage or applying an extractant solution, for the subsequent operations.

Preferably, the width of the isolation segments is 1 μm-5 mm. Preferably, the width of the isolation strips is 1 μm-5 mm.

Preferably, the width of each microwell is 1 μm-1 cm, more preferably 10 μm-2 mm. The length of each microwell is 1 μm-1 cm, more preferably 10 μm-2 mm.

Preferably, the thicknesses of the isolation segments, the isolation strips and the gel strips are 1 μm-1 cm, respectively, more preferably 10 μm-2 mm.

Preferably, the gel electrophoresis chip further comprises a plurality of first blocks arranged at one end of the first plurality of gel strips and respectively located between the gel strips. The first blocks are used for partitioning the proteins from IPG strips which undergo the first-dimensional electrophoresis to dispense the proteins in the second-dimension gel strip lanes. Preferably, the first blocks are triangular prisms.

Preferably, the gel electrophoresis chip further comprises a plurality of second blocks arranged at the other end of the first plurality of gel strips and respectively located between the gel strips. The second blocks are used to ensure smooth transition of the electric field in each gel strip.

Preferably, the gel electrophoresis chip further comprises a first contact zone in butt-joint connection with one end of the first plurality of gel strips. Preferably, the gel electrophoresis chip further comprises a second contact zone in butt-joint connection with the other end of the first plurality of gel strips. For example, in terms of horizontal electrophoresis, the first contact zone is, for example, stacking gel for disposing, for example, IPG strips and, for example, electrode buffer strips. The IPG strips are disposed in the same way as the conventional electrophoresis does, and the second contact zone is used for disposing, for example, electrode buffer strips. In terms of vertical electrophoresis, the first contact zone and the second contact zone may be reduced, even eliminated.

Preferably, the first substrate and the second substrate are made of one or more materials selected from an inorganic insulating material, an organic insulating material, a polymer insulating material and a composite material, preferably, a glass sheet, a quartz sheet, a silicon carbide sheet, a polymer sheet, or a silicon sheet coated with silicon dioxide or other insulating layers on the surface thereof.

In one embodiment of the present invention, a spare gel zone is further comprised, which can be used for being a lane of protein molecular weight markers and for disposing electrode buffer strips during protein or peptide mixture extraction.

The gel electrophoresis chip of the present invention is applicable to two-dimensional gel electrophoresis except diagonal electrophoresis, such as ISO-DALT (isoelectric focus-dalton weight) two-dimensional electrophoresis, IPG-DALT (immobilized pH gradient-dalton weight) two-dimensional electrophoresis, nonequilibrium pH gradient electrophoresis, blue native SDS polyacrylamide gel electrophoresis (BN/SDS-PAGE) and clear native SDS polyacrylamide gel electrophoresis (CN/SDS-PAGE), and has no limitation to first-dimension separation.

The gel electrophoresis chip is made by one or more selected from microelectromechanical processing technology, screen printing technology, 3D printing technology and lithography technology. High-precision production ensures the consistency and repeatability of the two-dimensional gel electrophoresis chip, thereby improving the reproducibility of two-dimensional gel electrophoresis analysis.

When applied to the conventional IPG-DALT two-dimensional gel electrophoresis, the operation method of the gel electrophoresis chip of the present invention is as follows:

1) First-dimensional electrophoresis (isoelectric focusing electrophoresis) using IPG strips: this step is the same as that of the conventional two-dimensional gel electrophoresis, that is, a protein sample is subjected to isoelectric focusing electrophoresis using the conventional IPG strips, to complete sample separation based on protein isoelectric points. The IPG strips may be prepared according to the conventional method or may be commercially available.

2) Second-dimensional electrophoresis using the gel electrophoresis chip: the protein sample in the IPG strips that is obtained by the first-dimensional electrophoresis of step 1) is subjected to equilibration and then transferred onto the gel electrophoresis chip of the present invention (for example, the first contact zone) for second-dimensional electrophoresis, to complete sample separation based on protein molecular weights.

3) In-gel digestion: the whole gel electrophoresis chip that is obtained by the second-dimensional electrophoresis of step 2) is subjected to in-gel digestion, that is, all the separated proteins in the biological sample on the electrophoresis chip undergo in-gel digestion at the same time. The method of sample preparation via in-gel digestion according to the present invention is the same as that via in-gel digestion of single protein spot in the prior art. The present invention applies reagents required to the chip surface by, for example, capillary dripping method (point matrix sample preparation), capillary spraying method, and automatic spraying method. Unlike the existing methods, in the present invention, all the protein spots are simultaneously digested in one digestion process to obtain peptide mixtures corresponding to all the separated proteins, which omits the steps of staining the separated proteins and excising gels and digesting one by one.

4) Extraction of peptide mixtures: by adding a peptide extractant solution or applying a voltage to the gel strips, the peptide mixtures in the gel strips are simultaneously transferred to the corresponding microwells, thereby achieving the purpose of simultaneously extracting the peptide mixtures of all the separated proteins. The direction of the voltage applied for extraction is parallel to the second direction along which the second plurality of isolation segments extend. The method of adding the peptide extractant solution is the same as that of applying a digestion reagent.

5) Preparation of mass spectrometry sample targets: the proteins or peptide mixtures are made into sample targets corresponding to different MS ionization methods. The MS ionization method includes but not limited to matrix-assisted laser desorption ionization (MALDI), desorption electrospray ionization (DESI), desorption atmospheric pressure photoionization (DAPPI), direct analysis in real time (DART), etc. Taking MALDI for example, a MALDI matrix solution is added to the microwells, all the proteins or peptide mixtures and the matrix are co-crystallized simultaneously, the proteins or peptide mixtures in all the microwells are made simultaneously into samples for MALDI MS analysis in one step, thereby completing the pretreatment of all proteins for MS analysis in one step. The method of adding the matrix is the same as that of applying a digestion reagent.

6) Ionization and mass spectrometry: the peptide mixtures or proteins in the microwells are ionized, and the resulting samples from ionization are subjected to MS analysis to obtain MS information. For example, peptide mass fingerprinting or peptide sequence tag may be obtained by MS analysis, and by protein database retrieval, the types of proteins in each microwell are identified or new proteins are found. The data of ion signal intensity of all the proteins and peptides in the microwells are combined to form a gel electropherogram, in which the MS data of each microwell is a pixel, which is similar to MALDI imaging technology.

The present invention has the following advantages:

1) The gel electrophoresis chip provided by the present invention can be applied to the second-dimensional electrophoresis of two-dimensional gel electrophoresis, with improvements of the conventional second-dimensional electrophoresis. The gel electrophoresis chip solves the problems of the conventional second-dimensional electrophoresis of two-dimensional gel electrophoresis and the sample preparation after second-dimensional electrophoresis, realizes protein separation and separation and in-gel digestion of all proteins at the same time, free of the steps of staining and gel excision. All the proteins or peptide mixtures can be simultaneously transferred from the gel strips to the corresponding microwells, free of one-by-one extraction. The preparation of MS samples with all the proteins or peptide mixtures in the microwells can be made at the same time, free of one-by-one treatment, thereby greatly shortening the time of preparing the samples for protein MS analysis, simplifying the operation, and making it possible to perform MS analysis on all the proteins. In short, the above operations in the prior art are time-consuming and laborious and difficult to realize full automation, and may cause mistakes and contamination. By comparison, the electrophoresis chip according to the present invention realizes high throughput and automation required for proteomic analysis.

2) The gel electrophoresis method according to the present invention can detect low-abundance proteins and increases the probability of finding target proteins of interest. The conventional pretreatment operation of MS analysis requires gel staining to visualize the positions of proteins, but any staining method has limitations to sensitivity and tendency of protein staining, and fails to visualize low-abundance proteins or proteins containing low content of dye-sensitive amino acids, resulting in detection errors. By comparison, the gel electrophoresis chip for gel electrophoresis according to the present invention does not require the above operation steps, and can treat all separated proteins at the same time to allow all separated proteins to be detected except the samples under the level of MS sensitivity.

3) The gel electrophoresis chip according to the present invention is made by microelectromechanical processing technology, screen printing technology, 3D printing technology, lithography technology and the like, has the features of high precision, good repeatability, wide selection range of manufacture materials and manufacture parameters, can separate and transfer proteins to microwells for free use, can be applied to various MS ionization techniques, can produce a digital two-dimensional gel electropherogram, can improve the reproducibility of two-dimensional gel electrophoresis, and can be used in most two-dimensional gel electrophoresis systems.

These features of the gel electrophoresis chip offer better prospects in proteomic analysis of biological samples.

BRIEF DESCRIPTION OF THE DRAWINGS

Hereinafter, the embodiments of the present invention will be described in detail with reference to the accompanying drawings.

FIG. 2b is a partially enlarged view of the gel electrophoresis chip as shown in FIG. 2a.

FIG. 3b is a cross-sectional view of FIG. 3a.

FIG. 4b is a cross-sectional view of FIG. 4a.

FIG. 5b is a cross-sectional view of FIG. 5a.

Figure 1:
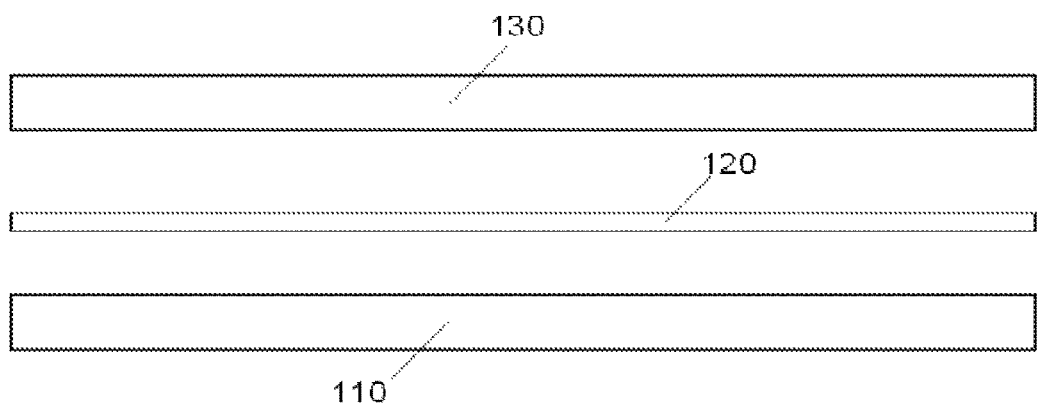
FIG. 1 is a cross-sectional view of a gel electrophoresis chip of the present invention.

In the figures, numeral 110 indicates first substrate, numeral 120 indicates microwell array, numeral 130 indicates second substrate, numeral 230 indicates first block, numeral 240 indicates second block, numeral 260 indicates first contact zone, numeral 270 indicates second contact zone, numeral 280 indicates spare gel zone, numeral 290 indicates spare gel zone, numerals 220, 320, 420, 520 indicate gel strips, numerals 210, 310, 410, 510 indicate isolation segments, numerals 311, 411, 412, 511, 512 indicate isolation strips, numerals 250, 350, 450, 550 indicate microwells, numerals 451, 452, 453, 552, 551 indicate openings.

DETAILED DESCRIPTION OF THE INVENTION

In order to illustrate the invention more clearly, the present invention will now be described in detail with reference to preferred embodiments and the accompanying drawings. For clarity and ease of understanding of the devices, the parts of the drawings are not drawn to scale. The like components in the drawings are denoted by the same reference numbers. Those skilled in the art should appreciate that the following detailed description is intended to be illustrative and not restrictive and should not be construed to limit the scope of the present invention.

Embodiment 1 Gel Electrophoresis Chip

FIG. 1 and FIG. 2 show a gel electrophoresis chip according to embodiment 1 of the invention, comprising a first substrate 110, and a plurality of parallel polyacrylamide gel strips 220 formed on the first substrate and respectively extending along a first direction. The width of the gel strips is 400 µm, and the distance between adjacent gel strips is 1 mm. Epoxy resin segments 210 are formed between adjacent gel strips and perpendicular to the gel strips, the width of which is 300 µm. The gel strips have substantially the same thickness as the epoxy resin segments, for example, being about 600 µm. The gel strips together with the epoxy resin segments form an array 120 of microwells having the size of 0.6 mm×0.7 mm, respectively. According to one implementation of the invention, a second substrate 130 is opposite to the first substrate 110 and in close contact with the gel strips 220 and the isolation segments (for example, epoxy resin segments 210).

According to one implementation of the invention, a plurality of first blocks 230 are arranged at one end of the first plurality of gel strips 220 and located between the gel strips, respectively. A plurality of second blocks 240 are arranged at the other end of the first plurality of gel strips 220 and located between the gel strips, respectively. In the implementation, each gel strip is gradually increasing its width at its two ends until the gel strips connect with each other. The first block and the second block are arranged in the region of gel strips having gradually-increasing width and have a triangular shape.

According to one implementation of the invention, the gel chip further comprises a first contact zone 260 formed at one end of the gel strip extending direction and in butt-joint connection with each of the gel strips 220. The contact zone is used for disposing the gel samples that have been separated by the first-dimensional electrophoresis. Preferably, the first contact zone has an end surface perpendicular to the gel strip extending direction. According to one implementation of the invention, the gel chip further comprises a second contact zone 270 formed at the other end of the gel strip extending direction and in butt-joint connection with each of the gel strips. The second contact zone, for example, is used for disposing electrode buffer strips. The first and second contact zones have the width of, for example, 2 cm.

According to one implementation of the invention, a spare gel region 280 and a spare gel region 290 are arranged on the left and right sides of the first plurality of gel strips 220, respectively.

In terms of a horizontal electrophoresis system, the first contact zone 260 is stacking gel and used for disposing cathode buffer strips and IPG strips during electrophoresis. The second contact zone 270 is used for disposing anode buffer strips during electrophoresis. The first blocks 230 are used to dispense the proteins from the IPG strips to the corresponding gel strips. The second blocks 240 are used to ensure smooth transition of the electric field in each gel strip. In terms of a vertical electrophoresis system, the first contact zone 260 and the second contact zone 270 may not exist.

After being separated in the gel strips 220, the proteins are applied with a voltage for extraction, so that all the proteins are simultaneously transferred from the gel strips 220 to the microwells 250 nearby. For the analysis of peptide mixtures of the proteins, all the separated proteins need to undergo in-gel digestion. The gel electrophoresis chip of the present invention can realize in-gel digestion of all the proteins in one digestion process, the resulting peptide mixtures from digestion are extracted by, for example, applying a voltage for extraction, so that all the peptide mixtures are simultaneously transferred from the gel strips to the corresponding microwells 250. Alternatively, a peptide extractant solution may be added to the microwells 250 in order to transfer the peptide mixtures into the corresponding microwells 250. By this extraction method, the peptide mixtures in the same one gel strip 220 are extracted and transferred to the microwells on both sides of the gel strip, that is, the peptide mixtures in two adjacent gel strips 220 are contained in the same one microwell 250.

Figure 2A:
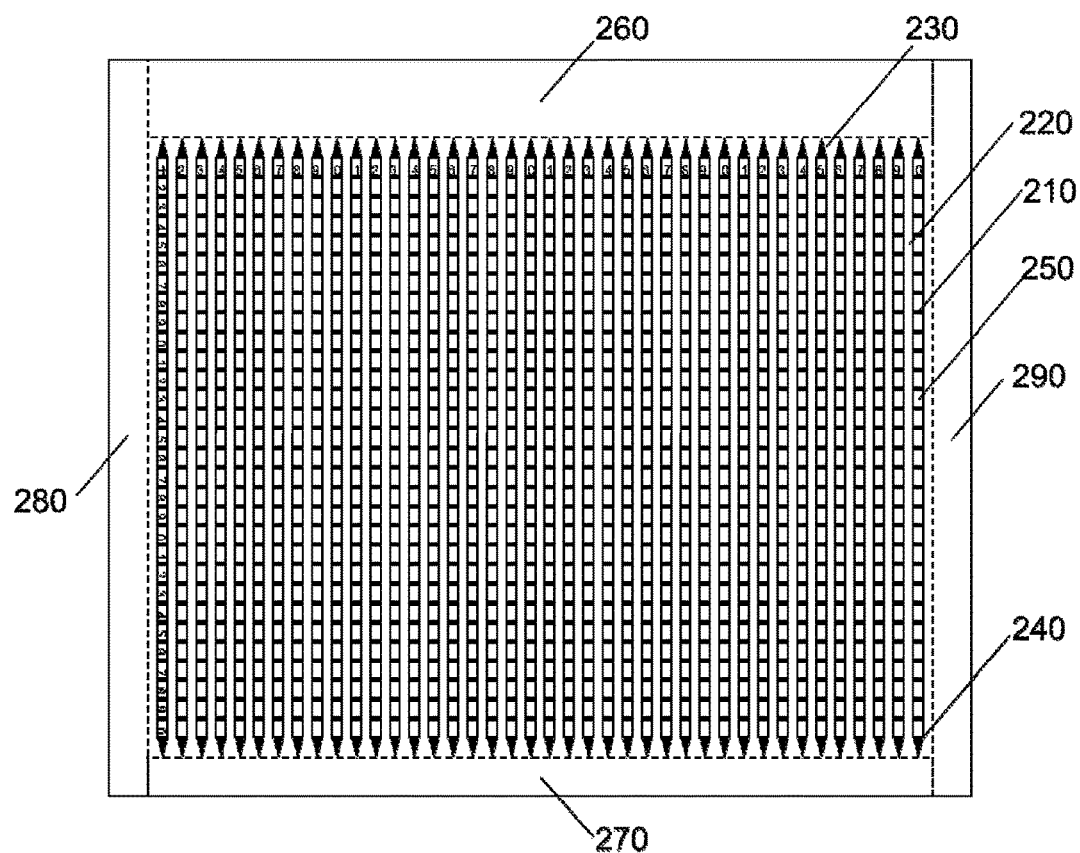
FIG. 2a is a schematic view of a microwell array region of a gel electrophoresis chip according to embodiment 1 of the present invention. The dashed lines are used to indicate different zones, not actual ones.
Figure 2B:
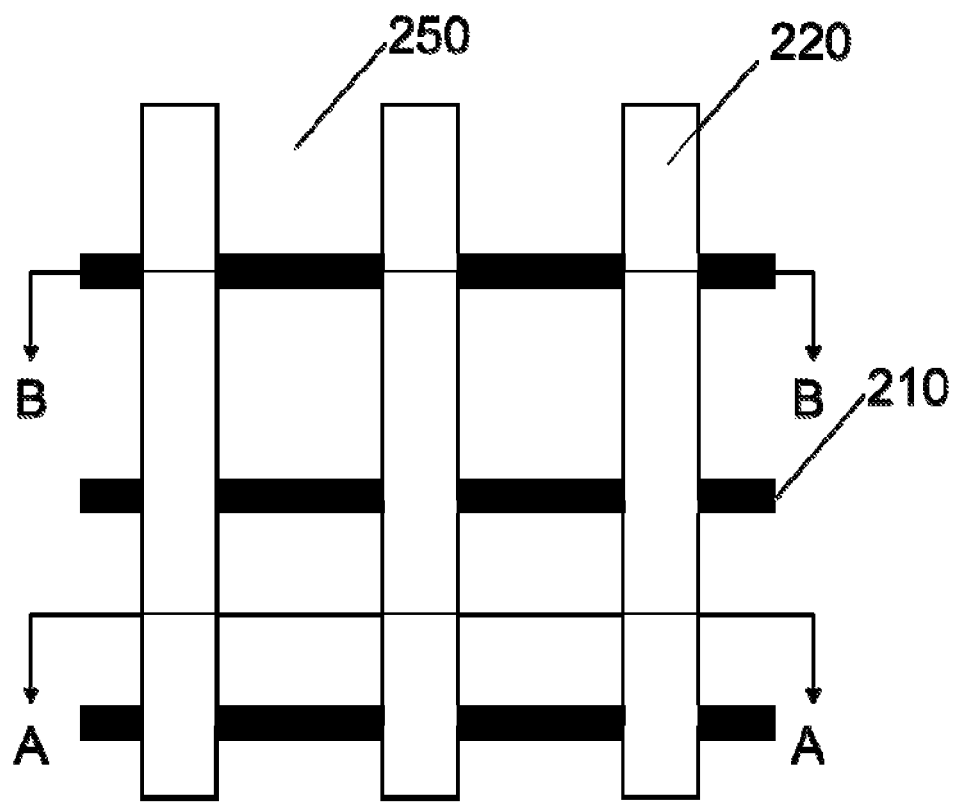
Figure 2C:
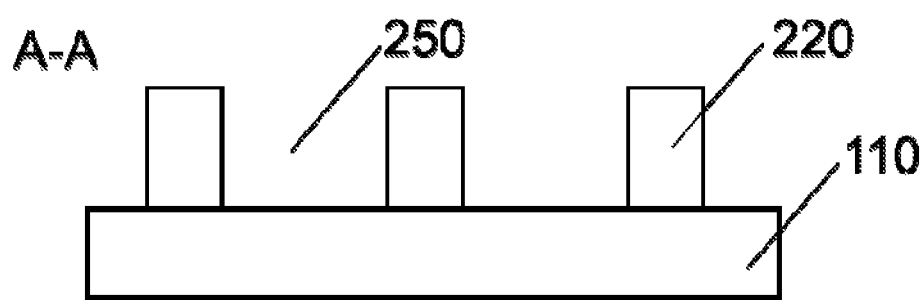
FIG. 2c is a cross-sectional view taken along line AA of FIG. 2b.
Figure 2D:
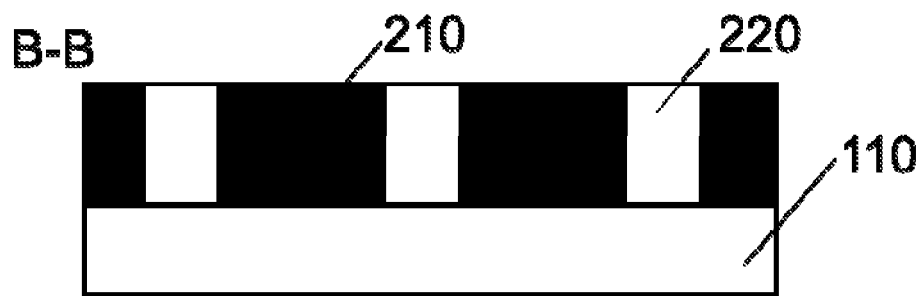
FIG. 2d is a cross-sectional view taken along line BB of FIG. 2b.

It should be noted that although the microwell 250 of FIG. 2 has a rectangular or square shape as shown in FIG. 2b-2d, there are no limitations to the microwell structure in the gel electrophoresis chip. Depending on different requirements for proteomic analysis, any one of microwell structure designs of FIG. 2-5, or other similar structure designs may be used. The number of gel strips, the number of epoxy resin segments and the number of microwells on one gel electrophoresis chip are not limited. 1200 (40×30=1200) microwells of FIG. 2 is exemplary and intended to be illustrative.

According to the gel electrophoresis chip of the embodiment, a polyacrylamide solution may be printed by the screen printing method. The solution is fully cured to form a gel, followed by printing epoxy resin isolation segments. The screen printing method is well known to those skilled in the art and will not be described herein.

Embodiment 2 Gel Electrophoresis Chip

Figure 3A:
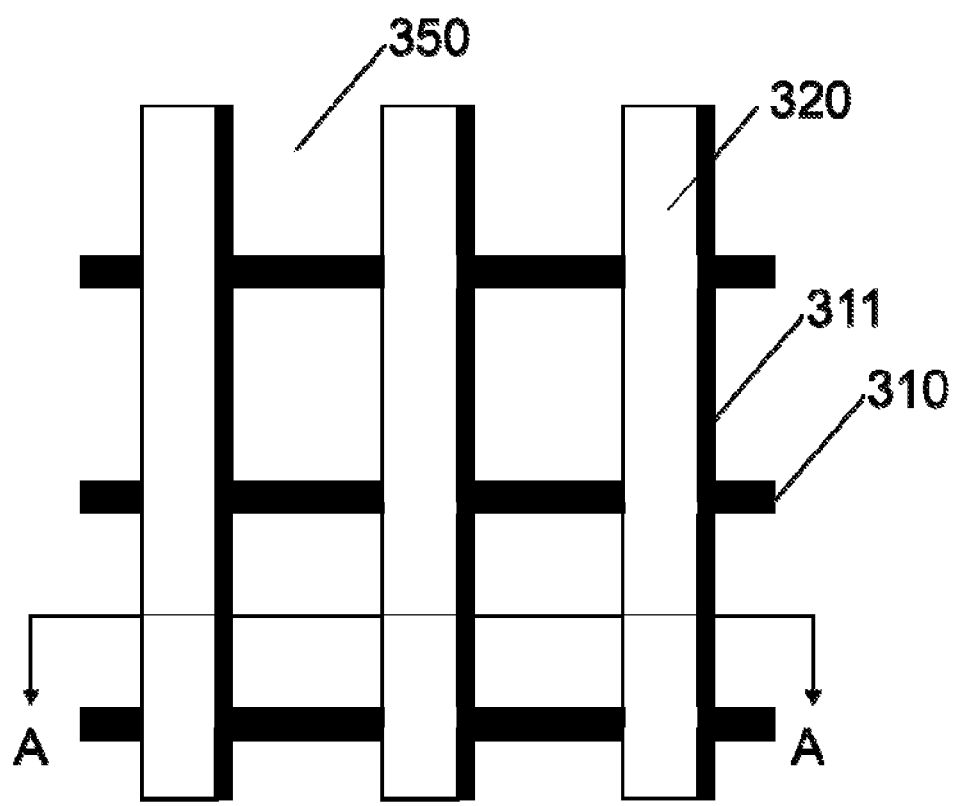
FIG. 3a is a partially enlarged view of the microwells of the gel electrophoresis chip of embodiment 2 of the present invention.
Figure 3B:
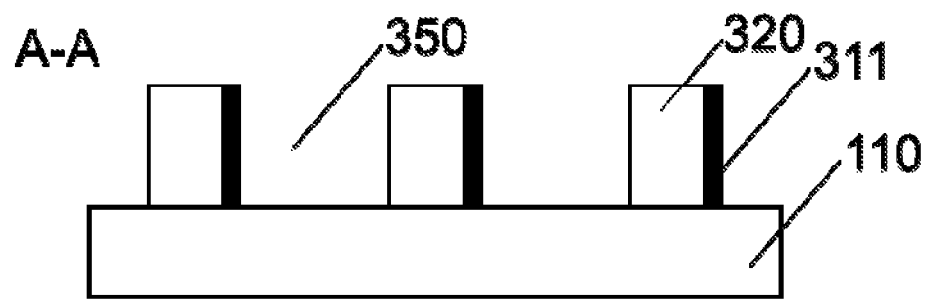
Figure 4A:
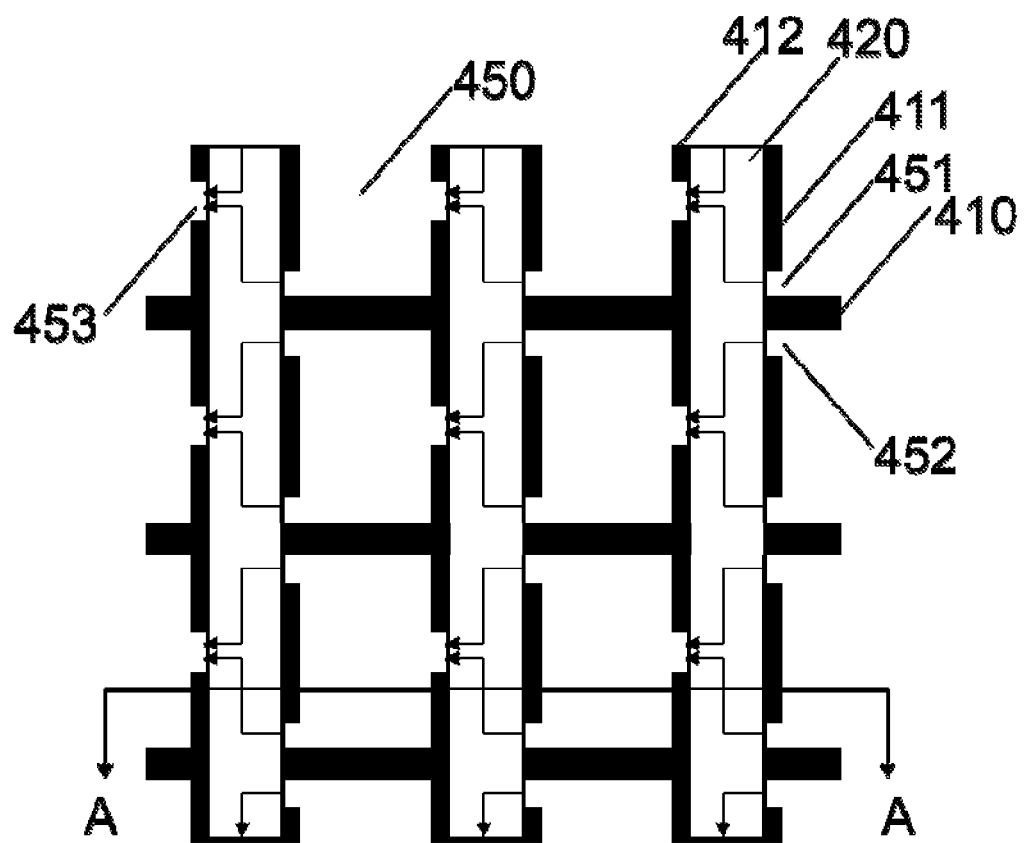
FIG. 4a is a partially enlarged view of the microwells of the gel electrophoresis chip of embodiment 3 of the present invention.
Figure 4B:
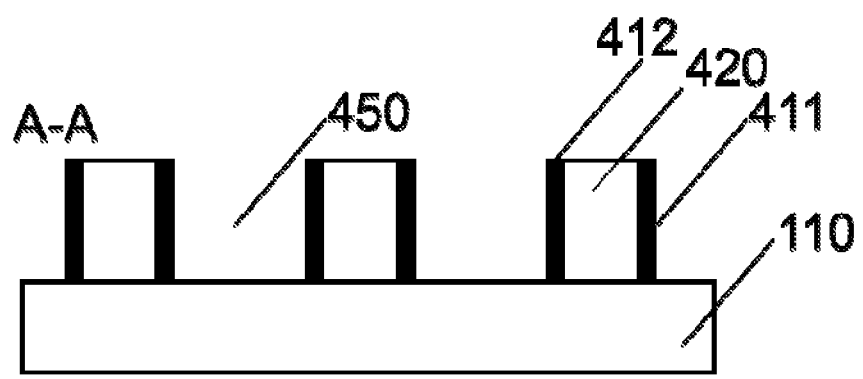
Figure 5A:
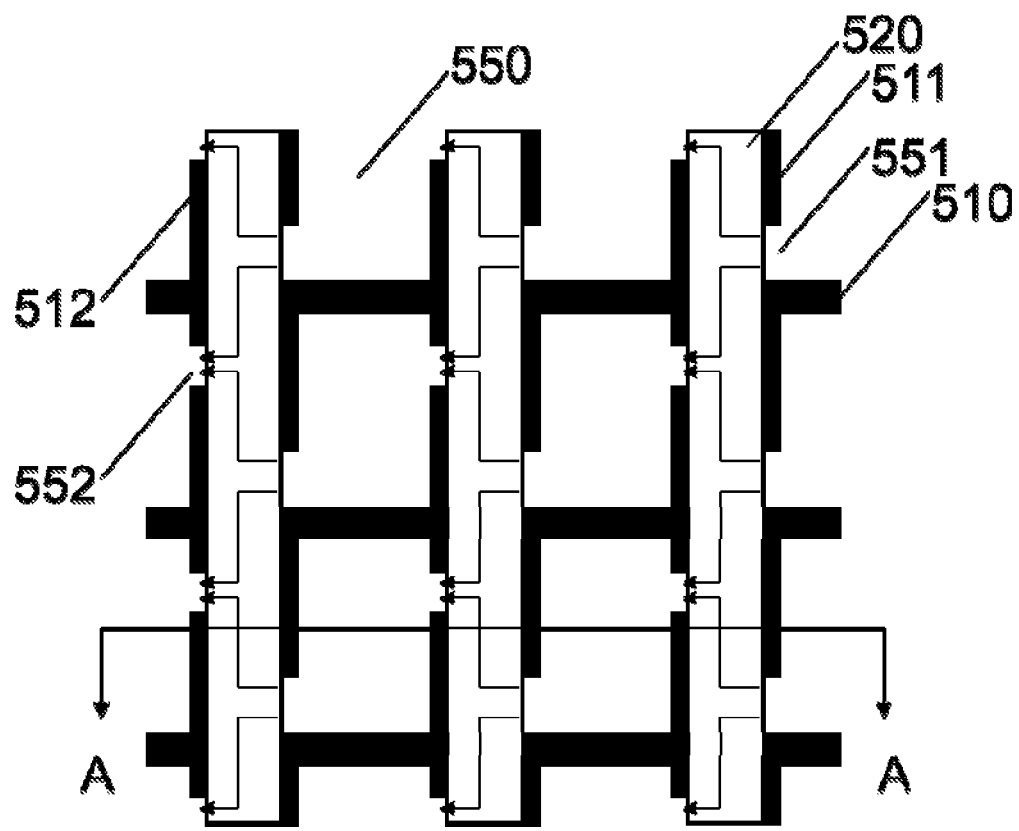
FIG. 5a is a partially enlarged view of the microwells of the gel electrophoresis chip of embodiment 4 of the present invention.
Figure 5B:
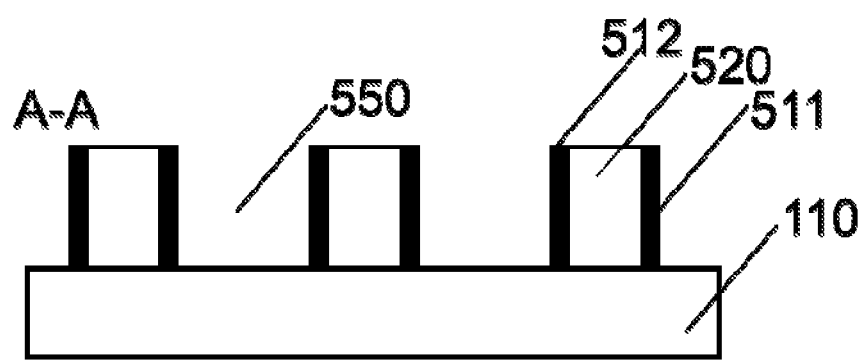

The gel electrophoresis chip of this embodiment is modified on the basis of embodiment 1, and further comprises high-density polyethylene isolation strips 311 arranged on the same side of the individual gel strips 320 and in contact with the gel strips 320. The isolation strips have substantially the same thickness as the gel strips, being 150 µm, and form microwells as shown in FIG. 3a.

Compared with the gel electrophoresis chip of embodiment 1, when extracting the peptides with the extractant solution, due to the addition of isolation strips, the protein components in each gel strip can only be extracted and transferred to the microwells remote from the side at which the isolation strip is located, which avoids the reduction of isoelectric focusing electrophoresis resolution caused by the conditions that the peptide mixtures in the same one gel strip 220 are extracted and transferred to the microwells on both sides of the gel strip and the peptide mixtures in two adjacent gel strips 220 are contained in the same one microwell 250, thereby improving the isoelectric focusing electrophoresis resolution.

However, such microwell design is unsuitable for extracting peptide mixtures or proteins by applying a voltage.

For the gel electrophoresis chip according to the embodiment, the high-density polyethylene isolation segments and isolation strips are made by the 3D printing method and then the polyacrylamide solution is printed and cured, getting ready for use. The 3D printing method is well known to those skilled in the art and will not be described herein.

Embodiment 3 Gel Electrophoresis Chip

The gel electrophoresis chip of this embodiment is modified on the basis of embodiment 1, with the difference in that: an isolation strip 411 and an isolation strip 412 are respectively arranged on both sides of each gel strip 420. The isolation strip is made of a photoresist, the same material as embodiment 1, and has substantially the same thickness as the gel strips. The isolation strip 411 forms two openings at each microwell 450, i.e. opening 451 and opening 452, the isolation strip 412 forms one opening at each microwell 450, i.e. opening 453.

Wherein, the openings 451, 452 and 453 may serve as current channels and the opening 453 may further serve as an exit for proteins or peptide mixtures during the extraction of proteins or peptide mixtures.

In the gel electrophoresis chip according to the embodiment, after the second-dimension separation of proteins, the proteins or peptide mixtures can be extracted by applying a voltage.

In the gel electrophoresis chip according to the embodiment, two different photoresists are applied by the photolithography method to form isolation segments and isolation strips, then the gel solution is injected between the isolation strips, and after the gel is cured, the photoresists at the openings are removed. The photolithography method is well known to those skilled in the art and will not be described herein.

Embodiment 4 Gel Electrophoresis Chip

The gel electrophoresis chip of this embodiment is modified on the basis of embodiment 1, with the difference in that: an isolation strip 511 and an isolation strip 512 are respectively arranged on both sides of each gel strip 520, wherein the isolation strip 511 forms one openings at each microwell 550, i.e. opening 551, and the isolation strip 512 forms one opening at each microwell 550, i.e. opening 552.

Wherein, the openings 551 and 552 may serves as current channels and the opening 552 may further serves as an exit for proteins or peptide mixtures during the extraction of proteins or peptide mixtures.

In the gel electrophoresis chip according to the embodiment, after the second-dimension separation of proteins, the proteins or peptide mixtures can be extracted by applying a voltage.

In the gel electrophoresis chips according to embodiment 3 and embodiment 4, the extraction of proteins or peptide mixtures by applying a voltage can enable most of the proteins or peptide mixtures that are separated in the gel to be extracted and transferred to the microwells, thereby increasing the extraction efficiency. Such gel electrophoresis chip has high resolution for a trace amount of proteins in a biological sample.

It is understood that the above embodiments of the present invention are merely illustrative for clearly describing the present invention and not intended to limit the embodiments of the invention, it will be apparent to those skilled in the art that other changes or variations may be made in the light of the above description, the present invention is not intended to be exhaustive of all embodiments, and any obvious changes or variations derived from the technical solution of the present invention still fall within the scope of the present invention.

What is claimed is:

1. A gel electrophoresis chip, comprising:
   a first substrate;
   a first plurality of gel strips formed on the first substrate, respectively extending along a first direction and having a certain width;
   a second plurality of isolation segments formed on the first substrate, respectively located between adjacent gel strips and extending along a second direction different from the first direction, the isolation segments being arranged to form a microwell array together with the gel strips.

2. The gel electrophoresis chip according to claim 1, wherein the second direction is perpendicular to the first direction.

3. The gel electrophoresis chip according to claim 1, further comprising a second substrate located on the gel strips and the isolation segments and in contact with the gel strips and the isolation segments.

4. The gel electrophoresis chip according to claim 1, further comprising a plurality of isolation strips respectively formed on the same side of the individual gel strips, in contact with the gel strips and having substantially the same thickness.

5. The gel electrophoresis chip according to claim 1, further comprising isolation strips formed on both sides of each gel strip, in contact with the gel strips and having substantially the same thickness, the individual isolation strips having at least one opening at each microwell.

6. The gel electrophoresis chip according to claim 1, wherein the gel strips are the gel strips for protein separation.

7. The gel electrophoresis chip according to claim 1, wherein the width of the gel strip is 1 µm-1 cm, and the thickness of the gel strips is 1 µm-1 cm.

8. The gel electrophoresis chip according to claim 1, wherein the isolation segments are made of one or more materials selected from an inorganic material, an organic material, and a composite material.

9. The gel electrophoresis chip according to claim 5, wherein the isolation strips are made of one or more materials selected from an inorganic material, an organic material, and a composite material.

10. The gel electrophoresis chip according to claim 1, wherein the width of the isolation segments is 1 µm-5 mm; and the thickness of the isolation segments is 1 µm-1 cm.

11. The gel electrophoresis chip according to claim 1, wherein the width of each microwell is 1 µm-1 cm, and the length of each microwell is 1 µm-1 cm.

12. The gel electrophoresis chip according to claim 5, wherein the width of the isolation strips is 1 µm-5 mm.

13. The gel electrophoresis chip according to claim 1, further comprising a plurality of first blocks arranged at one end of the first plurality of gel strips and respectively located between the gel strips.

14. The gel electrophoresis chip according to claim 13, further comprising a plurality of second blocks arranged at the other end of the first plurality of gel strips and respectively located between the gel strips.

15. The gel electrophoresis chip according to claim 1, further comprising a first contact zone in butt-joint connection with one end of the first plurality of gel strips.

16. The gel electrophoresis chip according to claim 15, further comprising a second contact zone in butt-joint connection with the other end of the first plurality of gel strips.

17. The gel electrophoresis chip according to claim 1, wherein the first substrate or the second substrate is made of a material selected from an inorganic insulating material, an organic insulating material, a composite material or combination thereof.

18. The gel electrophoresis chip according to claim 1, wherein the gel electrophoresis chip is made by one or more selected from microelectromechanical processing technology, screen printing technology, 3D printing technology and lithography technology.

19. A method of using the gel electrophoresis chip according to claim 1, comprising: performing, by using IPG strips, first-dimensional electrophoresis on a protein sample to be detected; performing, by using the gel electrophoresis chip, second-dimensional electrophoresis for the IPG strips that undergo the first-dimensional electrophoresis; transferring the proteins from the gel strips to the corresponding microwells by adding an extractant solution or applying a voltage to the gel strips; making sample targets with the proteins extracted in each of the microwells; and performing ionization and mass spectrometry (MS) analysis on the sample targets to obtain MS information.

20. A method of using the gel electrophoresis chip according to claim 1, comprising: performing, by using IPG strips, first-dimensional electrophoresis on a protein sample to be detected; performing, by using the gel electrophoresis chip, second-dimensional electrophoresis for the IPG strips that undergo the first-dimensional electrophoresis; performing in-gel digestion on the gel electrophoresis chip that undergoes the second-dimensional electrophoresis; transferring the peptides from the gel strips to the corresponding microwells by adding a peptide extractant solution or applying a voltage to the gel strips; making sample targets with the peptide mixture extracted in each of the microwells; and performing ionization and mass spectrometry (MS) analysis on the sample targets to obtain MS information.

* * * * *